United States Patent [19]

Trödel et al.

[11] Patent Number: 5,521,308
[45] Date of Patent: May 28, 1996

[54] PROCESS FOR THE PREPARATION OF CRYSTALLINE TACA

[75] Inventors: Reinhard Trödel, Hochheim am Main; Manfred Wieduwilt, Frankfurt am Main, both of Germany

[73] Assignee: Hoechst Aktiengesellschaft, Frankfurt am Main, Germany

[21] Appl. No.: 180,469

[22] Filed: Jan. 12, 1994

Related U.S. Application Data

[63] Continuation of Ser. No. 869,194, Apr. 14, 1992, abandoned, which is a continuation of Ser. No. 747,992, Aug. 21, 1991, abandoned.

[30] Foreign Application Priority Data

Aug. 23, 1990 [DE] Germany .................. 40 26 630.3

[51] Int. Cl.⁶ .................................. C07D 501/02
[52] U.S. Cl. .............................. 540/226; 540/227
[58] Field of Search ........................ 540/222, 226, 540/227

[56] References Cited

U.S. PATENT DOCUMENTS

| | | | |
|---|---|---|---|
| 4,376,200 | 3/1983 | Ozasa et al. | 540/226 |
| 5,126,445 | 6/1992 | Martin | 540/226 |

*Primary Examiner*—Nicholas Rizzo
*Attorney, Agent, or Firm*—Finnegan, Henderson, Farabow, Garrett & Dunner

[57] ABSTRACT

Process for the preparation of crystalline TACA

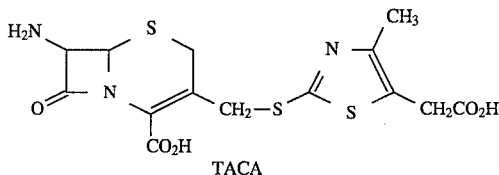

by reaction of 7-ACA

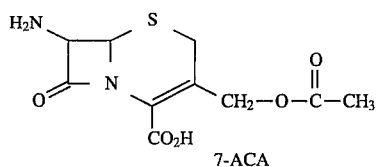

and MMTA

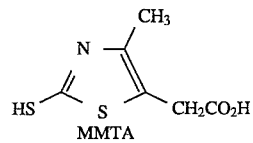

in the presence of a base and subsequent precipitation by addition of a TACA solution to a partial amount of an acid, which can also contain a precipitation auxiliary, and subsequent completion of the precipitation by further addition of acid or by further addition of TACA solution and acid.

12 Claims, No Drawings

PROCESS FOR THE PREPARATION OF CRYSTALLINE TACA

This application is a continuation of application Ser. No. 07/869,194, filed Apr. 14, 1992, now abandoned, which was a continuation of application Ser. No. 07/747,992, filed Aug. 21, 1991, abandoned.

The present invention relates to a crystallization process for the isolation of 7-β-amino-3- (5-carboxy-methyl-4 -methyl-1,3-thiazol-2-yl-thiomethyl)-ceph-3-em-4-carboxylic acid (TACA) of the formula

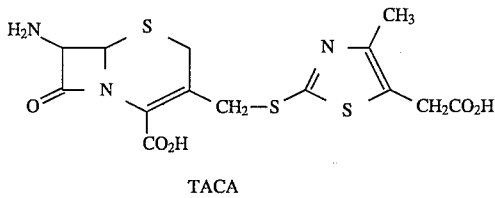

TACA

TACA is the central intermediate in the preparation of the human antibiotic cefodizime

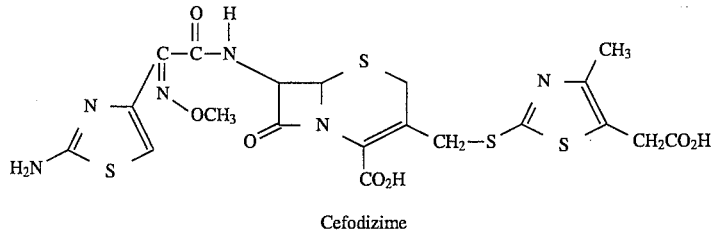

Cefodizime which is obtained by acylation of TACA. Cefodizime is employed against bacterial infections as the sterile disodium salt.

The preparation of TACA by reaction of 7-aminocephalosporanic acid (7-ACA)

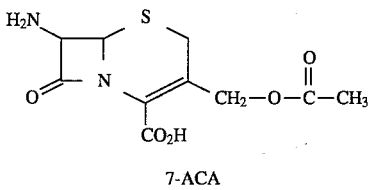

7-ACA and 2-mercapto-4-methyl-5-carboxymethyl-1,3-thiazole

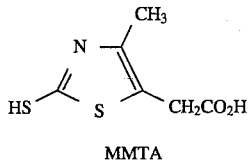

MMTA in water in the presence of a base (sodium bicarbonate) and precipitation by addition of an acid (2N hydrochloric acid, pH 2.0) is described in U.S. Pat. No. 4,278,793. The MMTA radical is introduced here by a replacement reaction in the side chain of the 7-ACA and TACA is thus formed. It is expedient in order to precipitate the TACA to add not only acid, but also a precipitation aid, preferably an alcohol. The crystallizate thus obtained is then centrifuged in a customary manner, washed in the centrifuge, isolated and dried.

This process, which is known from the literature in principle, in which the precipitation of the TACA is carried out by addition of an acid, was checked on the laboratory and technical scale and in its possibility of large scale application, a customary chromatographic purification step also being inserted.

On the laboratory and technical scale, the precipitation of the TACA can be carried out in such a way that the solution of the TACA, which, due to the preparation, is present as a salt, preferably the sodium salt, and is purified by means of an adsorption chromatography column, is first treated with a precipitation auxiliary, for example an alcohol, preferably n-butanol. If an acid is now added, preferably an inorganic acid, preferably sulfuric acid, and a homogeneous phase is produced by stirring, the solution, which is supersaturated with TACA, remains initially clear until, after some time, crystallization begins.

The crystallizate thus obtained can indeed be separated from its mother liquor with the aid of a centrifuge, washed and isolated on the scale of a few kilograms, but not on the large scale in an acceptable time without loss of quality. As a way out, the only possibility in the case of this crystallization procedure is to reduce the batch size drastically in order, as a result of the then considerably smaller batch size, to have such a small layer thickness of crystallizate in the centrifuge that the entire isolation process is possible in an acceptable period of time without loss of quality.

In the context of large-scale process development for the preparation of TACA, a method was worked out to precipitate TACA from the solution as a crystallizate. However, this method leads—as is shown below—in the case of a large-scale production quantity to the isolation time for the crystallizate in a centrifuge lasting so long that distinct damage to the product with respect to color, content and yield already occurs.

In this method, the precipitation was carried out in such a way that, after replacement by MMTA in the 3'-position of 7-ACA to give TACA, the TACA reaction solution was purified by means of a chromatography column packed with adsorption resin, preferably HP 20. The product-containing eluate fraction was treated with a precipitation auxiliary, in particular an alcohol, preferably n-butanol. Within a certain time, preferably about 30 minutes, a defined pH of preferably about 5.5 was established by addition of an acid, preferably an inorganic acid, in particular of about 15% strength sulfuric acid. The TACA began to crystallize during this addition or shortly thereafter.

The mixture was subsequently stirred for a short time, preferably about 15 minutes, and then a defined final pH of preferably about 4.0 was established by further addition of the acid. The mixture was subsequently stirred for some time, preferably about 1 hour, and the suspension was added to a centrifuge. The mother liquor was removed by centrifugation at a moderate speed, preferably 300–400 rpm, and the crystal cake which remained was washed with wash liquid, preferably an alcohol, in particular isopropanol. After centrifugal drying at the same speed, preferably about 400 rpm, the solid was isolated and dried.

These processes lasted more than 30 hours on a scale of about 100 kg of product/batch (this corresponds to one centrifuge filling). At the same time, an increasing discoloration of the solid was observed, such that the dried TACA no longer complied with the quality criteria set. The batch was therefore unusable for further processing.

There was thus a need to find a crystallization process which allows the crystallization, centrifugation, washing and isolation of TACA on a large scale without losses in quality occurring during the time necessary for this.

The present invention therefore relates to a process for the preparation of crystalline TACA

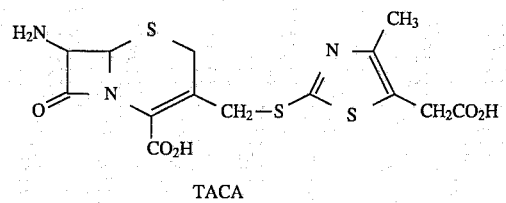

TACA by reaction of 7-ACA

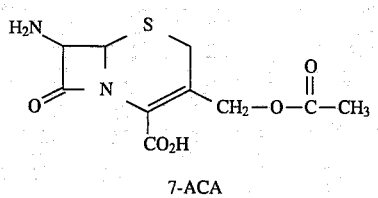

7-ACA and MMTA

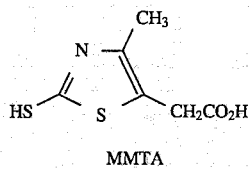

MMTA in the presence of a base and subsequent precipitation of the TACA by addition of an acid, which comprises precipitating the TACA by addition of a TACA solution to a partial amount of the acid, which can also contain a precipitation auxiliary, the precipitation being completed by further addition of acid up to a final pH of 3.0–4.5 or, if the final pH is kept constant, by further addition of TACA solution and acid.

By means of the present invention, the manner of the crystallization is modified by agglomeration of finely crystalline material ("inverse crystallization") such that the TACA can subsequently be centrifuged in a centrifuge and washed, and also isolated, on the large scale in an acceptable time without loss of quality. This material maintains the quality criteria set and is very highly suitable for further processing.

The precipitation auxiliary, in particular a low molecular weight alcohol, preferably n-butanol or amyl alcohol, is initially introduced together with a partial amount, preferably about 40–50%, of the total amount of acid calculated for the conversion of the TACA salt, preferably of the sodium salt, into the free carboxylic acid. The calculation is carried out with reference to the content of TACA in the eluate to be determined previously in each case. Suitable acids are inorganic acids, such as, for example, hydrochloric acid or preferably sulfuric acid, in particular about 15% strength sulfuric acid, or organic acids, such as, for example, formic acid or acetic acid.

The previously collected eluate fractions, obtained by means of an adsorption resin, preferably HP 20, are added with stirring in the course of a short time, preferably about 15 minutes. In the course of this, crystallization begins immediately and the pH increases to a value of preferably about 5.3 to 5.4. After stirring for a short time, preferably about 5 minutes, the final pH of about 3.0–4.5, in particular 3.8–4.2, preferably 4.0, is established by further addition of acid, preferably in the course of about 10 minutes. The mixture is subsequently stirred for a short time, preferably about 5 minutes, and allowed to settle for a longer time, preferably about 1.5 hours, without stirring. It is then possible to syphon off a relatively large part, about ⅓ to ½ of the mother liquor, as a clear supernatant above the suspension. This syphoned-off part, as it only contains a little very fine solid, is not added via the centrifuge. The remaining suspension containing the crystallizate is then added to a centrifuge. The mother liquor is removed by centrifugation at a moderate speed, preferably about 300–400 rpm, and the crystal cake which remains is washed with wash liquid, preferably an alcohol, preferably isopropanol. After centrifugal drying at the same speed, preferably about 400 rpm, the solid is isolated and dried.

These processes last less than 6 hours on a scale of about 100 kg of product/batch (this corresponds to one centrifuge filling). At the same time, no discoloration of the solid is observed. The dried TACA complies with the quality criteria set and is therefore highly suitable for further processing to cefodizime.

The process according to the invention can also be carried out with slight modifications. Thus, it is even possible to dispense entirely with the precipitation auxiliary and only to initially introduce the partial amount of the acid, or even to replace the inorganic acid by an organic acid, such as, for example, formic acid, for example 18% strength formic acid or acetic acid. The inverse crystallization method can also be modified such that, after initially introducing a partial amount of the acid and, if desired, a precipitation auxiliary, eluate is added and after attaining and while further maintaining the final pH defined above, still further eluate and the residual acid are added at the same time.

The process according to the invention with its variants results in it being possible to isolate the TACA on a large scale in the period of time necessary for this without loss of quality. The large-scale preparation of TACA on a scale of about 100 kg of product/batch has therefore only become possible at all. Since the addition of acid, which was customary hitherto, to precipitate the TACA gave poor results, it was not to be expected that the addition of a partial amount of the acid essential according to the invention would lead to such surprising results.

The following exemplary embodiments serve to illustrate the process according to the invention further, without restricting it thereto.

EXAMPLE 1

Preparation of the TACA-containing eluate 486 ml of demineralized water are initially introduced into a 2000 ml four-necked flask with nitrogen blanketing and 22.8 g (0.120 mol) of mercaptomethylthiazoleacetic acid (MMTA) are introduced with stirring. The MMTA is dissolved at pH 6.3 to 6.6 in the course of about 10 minutes by dropwise addition of about 14.1 g (10.2 ml) of sodium hydroxide solution (33% strength). The solution is then heated to 70° C.

In the meantime, 28.61 g (0.100 mol) of 7-aminocephalosporanic acid (7-ACA) are stirred in a 250 ml beaker with 97.9 ml of demineralized water to give a homogeneous suspension. The 7-ACA suspension is metered into the MMTA solution in the course of about 55 minutes using a metering pump. The internal temperature is kept at 70° C. in the course of this. At the same time as the metering, the pH of the reaction solution is kept at pH 6.3 to 6.4 by metering in altogether about 240 g (225 ml) of sodium hydrogen carbonate solution (8% strength).

After metering is complete, the 7-ACA vessel is rinsed out with 22 ml of demineralized water and the rinsed water is added to the reaction solution. To complete the reaction, the reaction mixture is subsequently stirred at 70° C. for one hour.

Purification:

After reaction is complete, the solution is cooled to 30° C. and pumped at 3 BV/h through a column containing 300 ml of adsorption resin HP 20.

The first three hundred milliliters of the eluate (forerun) are discarded. The remaining eluate is collected. After metering of the reaction solution is complete, the column is rinsed with 700 ml of demineralized water (v=3 BV/h) and the wash eluate is combined with the product eluate.

Precipitation:

The eluate collected is initially introduced into a 2000 ml four-necked flask and treated with 72.5 g (89.5 ml) of n-butanol. Using altogether about 83 ml of sulfuric acid (15% strength), the mixture is first adjusted to pH 5.5 (35 ml) in the course of about 30 minutes, subsequently stirred for about 15 minutes, then further adjusted to pH 4.0 (48 ml) in the course of about 30 minutes while slowly stirring at 25° to 30° C. and subsequently stirred at 20° C. to 25° C. for about one hour. The precipitate is then filtered off with suction, washed with 250 ml of demineralized water and 250 ml of 2-propanol and dried overnight at room temperature in vacuo.

Weight of precipitate: 30.59 g

Regeneration of the adsorption resin column:

250 ml of sodium hydroxide solution (1N) and 250 ml of 2-propanol are initially introduced into a heatable vessel, and are heated to 70° C. and pumped through the adsorption column at 1BV/h. The column is then washed with 500 ml of demineralized water and 1000 ml of acetic acid (1% strength) until a pH of 5 to 7 is attained in the column effluent. The column is back-rinsed with about 250 ml of demineralized water and allowed to settle overnight.

EXAMPLE 2

44.0 ml of sulfuric acid (15% strength) and 69.5 ml of n-butanol are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 41.0 ml of sulfuric acid (15% strength) and the resulting crystal suspension is subsequently stirred at 20° to 25° C. for one hour. The solid is filtered off, washed with 250 ml of demineralized water and 250 ml of 2-propanol and dried overnight at room temperature in vacuo.

Weight of precipitate: 30.90 g

EXAMPLE 3

39.5 ml of sulfuric acid (15% strength) are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 40.1 ml of sulfuric acid (15% strength) and the resulting crystal suspension is subsequently stirred at 20° to 25° C. for about one hour. The solid is filtered off, washed with 250 ml of demineralized water and 250 ml of 2-propanol and dried overnight at room temperature in vacuo.

Weight of precipitate: 29.41 g

EXAMPLE 4

43.0 ml of formic acid (18% strength) are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 47.1 ml of formic acid and the resulting crystal suspension is subsequently stirred at 20° to 25° C. for about one hour. The solid is filtered off, washed with 250 ml of demineralized water and 250 ml of 2-propanol and dried overnight at room temperature in vacuo.

Weight of precipitate: 30.40 g

EXAMPLE 5

43.0 ml of formic acid (18% strength) and 69.5 ml of n-butanol are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 50.0 ml of formic acid (18% strength) and the resulting crystal suspension is subsequently stirred at 20° to 25° C. for about one hour. The solid is filtered off, washed with 250 ml of demineralized water and 250 ml of 2-propanol and dried overnight at room temperature in vacuo.

Weight of precipitate: 29.87 g

EXAMPLE 6

37.0 ml of acetic acid (99.8% strength) are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 38.7 ml of acetic acid (99.8% strength) and the resulting crystal suspension is subsequently stirred for about one hour at 20° to 25° C. The solid is filtered off, washed with 250 ml of demineralized water and 250 ml of 2-propanol and dried overnight at room temperature in vacuo.

Weight of precipitate: 30.30 g

EXAMPLE 7

37.0 ml of acetic acid (99.8% strength) and 69.5 ml of n-butanol are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 54.0 ml of acetic acid (99.8% strength) and the resulting crystal suspension is subsequently stirred at 20° to 25° C. for about one hour. The solid is filtered off, washed with 250 ml of demineralized water and 250 ml of 2-propanol and dried overnight at room temperature in vacuo.

Weight of precipitate: 30.47 g

EXAMPLE 8

40.0 ml of sulfuric acid (15% strength) and 69.5 ml of amyl alcohol (mixture of 70% n- and 30% isoamyl alcohol) are initially introduced into a 2000 ml four-necked flask. TACA column eluate prepared analogously to Example 1 is metered in with stirring in the course of about 5 minutes. After a subsequent stirring time of about 5 minutes, the mixture is adjusted to pH 4.0 using a further 42.0 ml of sulfuric acid (15% strength) and the resulting crystal suspension is subsequently stirred at 20° to 25° C. for about one hour. The solid is filtered off, washed with 250 ml of demineralized water and 250 ml of 2-propanol and dried overnight at room temperature in vacuo.

Weight of precipitates 30.60 g

EXAMPLE 9

35.0 ml of sulfuric acid (15% strength) are initially introduced into a 2000 ml four-necked flask. TACA column eluate prepared analogously to Example 1 is metered in with stirring in the course of about 5 minutes. As soon as pH 4.0 is attained, 43.0 ml of sulfuric acid (15% strength) are simultaneously metered in in such a way that a pH of 4.0 is maintained. The resulting crystal suspension is subsequently stirred at 20° to 25° C. for about one hour. The solid is filtered off, washed with 250 ml of demineralized water and 250 ml of 2-propanol and dried overnight at room temperature in vacuo.

Weight of precipitate: 30.81 g

EXAMPLE 10

35.0 ml of sulfuric acid (15% strength) and 69.5 ml of n-butanol are initially introduced into a 2000 ml four-necked flask. TACA column eluate prepared analogously to Example 1 is metered in with stirring in the course of about 5 minutes. As soon as pH 4.0 is attained, 50.0 ml of sulfuric acid (15% strength) are simultaneously metered in in such a way that a pH of 4.0 is maintained. The resulting crystal suspension is subsequently stirred at 20° to 25° C for about one hour. The solid is filtered off, washed with 250 ml of demineralized water and 250 ml of 2-propanol and dried overnight at room temperature in vacuo.

Weight of precipitate: 30.98 g

We claim:

1. A process for preparing crystalline TACA

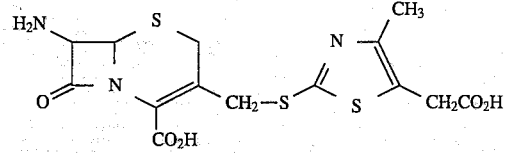

which comprises the steps of:
reacting 7-aminocephalosporanic acid with 2-mercapto-4-methyl-5-carboxymethyl-1,3-thiazole in the presence of a base to form a solution of TACA,
adding the TACA solution to less than one equivalent of an acid to initiate precipitation of the TACA from the solution, and
completing precipitation by adding additional acid.

2. The process of claim 1, wherein the step of completing precipitation further includes adjusting the pH to a range of 3.0–4.5.

3. The process of claim 1, wherein the precipitation is completed by holding the pH constant and adding TACA solution with the additional acid.

4. The process of claim 1, further comprising the use of a precipitation auxiliary in the adding step.

5. The process of claim 4, wherein the precipitation auxiliary comprises an alcohol.

6. The process of claim 5, wherein the alcohol is n-butanol or amyl alcohol.

7. The process of claim 1, wherein the TACA solution is an eluate obtained from an absorption resin.

8. The process of claim 1, wherein the amount of acid ranges from 0.4–0.5 equivalents.

9. The process of claim 1, wherein the acid is an organic or inorganic acid.

10. The process of claim 9, wherein the inorganic acid is hydrochloric or sulfuric acid and the organic acid is formic or acetic acid.

11. The process of claim 2, wherein the pH is adjusted to a range from about 3.8–4.2.

12. The process of claim 1, further comprising centrifuging the crystalline TACA to form a crystal cake, washing the crystal cake of TACA, and centrifugally drying the washed crystal cake.

* * * * *